US009585610B2

(12) United States Patent
Terasawa et al.

(10) Patent No.: US 9,585,610 B2
(45) Date of Patent: Mar. 7, 2017

(54) MEDICAL NEEDLE

(71) Applicant: Terumo Kabushiki Kaisha, Tokyo (JP)

(72) Inventors: Yuya Terasawa, Chuo (JP); Junichi Otsu, Ichikawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 198 days.

(21) Appl. No.: 14/490,454

(22) Filed: Sep. 18, 2014

(65) Prior Publication Data

US 2015/0005666 A1 Jan. 1, 2015

Related U.S. Application Data

(63) Continuation of application No. PCT/JP2013/055403, filed on Feb. 28, 2013.

(30) Foreign Application Priority Data

Mar. 21, 2012 (JP) .................................. 2012-063020

(51) Int. Cl.
*A61B 5/15* (2006.01)
*A61M 5/158* (2006.01)
*A61M 5/32* (2006.01)

(52) U.S. Cl.
CPC ....... *A61B 5/150641* (2013.01); *A61M 5/158* (2013.01); *A61M 5/326* (2013.01);
(Continued)

(58) Field of Classification Search
CPC ............ A61B 5/1433; A61B 5/150641; A61B 5/150656; A61B 5/15074; A61M 5/3232;
(Continued)

(56) References Cited

U.S. PATENT DOCUMENTS 5,928,199 A 7/1999 Nakagami
7,294,118 B2 * 11/2007 Saulenas ........... A61M 25/0637
604/110

(Continued)

FOREIGN PATENT DOCUMENTS

JP 03-134920 B2 2/2001
JP 2001-309976 A 11/2001
(Continued)

OTHER PUBLICATIONS

International Search Report dated Jun. 4, 2013 issued in Application No. PCT/JP2013/055403.

*Primary Examiner* — Devin Henson
*Assistant Examiner* — Audrey J Parker
(74) *Attorney, Agent, or Firm* — Foley & Lardner LLP

(57) ABSTRACT

A medical needle includes a needle body including a needle tip on a front end of the needle body; a shaft provided on a base end of the needle body; a housing pipe including a first tube, and a second tube; and a lock member that includes at least one engaging unit that is releasably engaged with the shaft, and at least one engagement release unit. The shaft is slidable from a first position at which the front end of the needle body protrudes from the housing pipe by a predetermined length, to a second position at which the front end of the needle body is located in the housing pipe. Engagement of the at least one engaging unit with the shaft is releasable by pressing the at least one engagement release unit inward.

19 Claims, 7 Drawing Sheets

(52) U.S. Cl.
CPC ........ *A61M 5/3216* (2013.01); *A61M 5/3243* (2013.01); *A61M 5/3257* (2013.01); *A61M 2005/1586* (2013.01)

(58) Field of Classification Search
CPC ........ A61M 5/3257; A61M 2005/3246; A61M 2005/3258; A61M 5/3243
See application file for complete search history.

(56) References Cited

U.S. PATENT DOCUMENTS

| | | | |
|---|---|---|---|
| 8,708,969 B2* | 4/2014 | Carlyon | A61M 5/3257 604/163 |
| 9,044,552 B2* | 6/2015 | Schraga | A61M 5/158 |
| 9,227,012 B2* | 1/2016 | Fujii | A61M 5/158 |
| 2001/0027292 A1 | 10/2001 | Tamura et al. | |
| 2003/0078540 A1 | 4/2003 | Saulenas et al. | |

FOREIGN PATENT DOCUMENTS

| | | |
|---|---|---|
| JP | 2001-346875 A | 12/2001 |
| JP | 2003-180829 A | 7/2003 |

* cited by examiner

MEDICAL NEEDLE

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/055403 filed on Feb. 28, 2013, which is based upon and claims the benefit of priority of Japanese Application No. 2012-063020 filed on Mar. 21, 2012, the entire contents of which are hereby incorporated by reference in their entireties.

BACKGROUND

Technical Field

The present disclosure relates to a medical needle used, for example, for blood collection, blood transfusion, or fluid infusion.

Background Art

A medical needle that is used, for example, for blood collection, blood transfusion, or fluid infusion while being connected, for example, to a blood collection device, a blood transfusion set, or a fluid infusion set of a blood bag or a blood processing circuit (such as an apheresis circuit, or a hemodialysis circuit) is known. The medical needle described above generally includes a needle body having a sharp needle tip on the front end, and a hub provided on the base end of the needle body. When a used medical needle is disposed, it is necessary to cover the needle body in order to prevent the person who disposes the needle from carelessly touching the needle body. In light of the foregoing, a medical needle including a protector capable of covering the used needle body has been proposed (e.g., refer to JP 3134920 B1).

The winged indwelling needle (medical needle) disclosed in JP 3134920 B1 includes a cannula (needle body), a hub provided on the base end of the cannula, and a holding pipe (protector) configured to house and hold the hub therein. The front end of the cannula supported with the hub can slide from a first position in which the front end of the cannula protrudes from the front end of the holding pipe to a second position in which the front end of the cannula is housed in the holding pipe along the inner wall of the holding pipe. A first engaging unit configured to releasably seize the hub at the first position of the holding pipe and a second engaging unit configured to substantially unreleasably seize the hub at the second position of the holding pipe are provided between the hub and the holding pipe.

When the medical needle is used, the user holds the trunk (the holding pipe in JP 3134920 B1) of the medical needle with the fingers to insert the needle body into the patient's skin. In that case, if the trunk of the medical needle has an appropriate small diameter, it is easy to stabilize the needle tip because the user readily holds the trunk. Also, it is easy to accurately insert the needle into a hard blood vessel or a thin blood vessel.

However, when the winged indwelling needle disclosed in JP 3134920 B1 is used, the front end of the hub is inserted into the position of the front end of the holding pipe. This makes it difficult to narrow the holding pipe that is the trunk.

SUMMARY OF INVENTION

In light of the foregoing, one objective of certain embodiments of the present invention is to provide a medical needle in which the trunk is narrowed in order to, for example, improve the operability.

According to one embodiment, a medical needle includes: a needle body including a needle tip on a front end of the needle body; a shaft provided on a base end of the needle body; a housing pipe including a first tube, and a second tube that is provided on a base end of the first tube and in which the shaft is placed displaceably in an axial direction; and a lock member that includes engaging units releasably engaged with the shaft, and engagement release units protruding to an outside of the housing pipe through side holes provided on the housing pipe, and that is fixed in the housing pipe. The shaft can slide on the housing pipe from a first position at which the front end of the needle body protrudes from the housing pipe by a predetermined length and the front end of the shaft is placed in the second tube to a second position at which the front end of the needle body is housed in the housing pipe. Engaging the engaging units with the shaft holds the shaft at the first position on the housing pipe. Engagement of the engaging units with the shaft is released when the engagement release units are pressed inward.

In the structure described above, because the front end of the shaft is placed nearer to the base-end side than to the first tube of the housing pipe in the second tube when the shaft is placed in the most front-end side in the range of motion, it is easy to form the first tube of the housing pipe to be narrow. In other words, because the shaft is not inserted in the first tube forming the front-end side of the housing pipe, the outer diameter of the first tube can be reduced. This can easily reduce the diameter of the trunk of the medical needle. The user easily holds the narrowed trunk with the fingers. This can provide the medical needle with good operability. Furthermore, in certain embodiments of the present invention, the structure in which the lock member is placed not on the base end of the housing pipe but nearer to the front-end side than to the base end (an intermediate portion in the axial direction of the housing pipe) is adopted. This prevents the entire length of the medical needle from increasing in spite of the structure in which the front end of the shaft is placed nearer to the base-end side in comparison with a conventional technique. As described above, the medical needle according to the present invention can improve operability by narrowing the trunk without increasing the entire length.

In one aspect, the lock member includes a base unit held and fixed on an inner surface of the housing pipe, and an elastically deformable arm unit protruding from the base unit. The engaging units and the engagement release units are provided on the arm unit. When the engagement release units are pressed inward, displacement of the engaging units in a direction away from the shaft can release the engagement of the engaging units with the shaft.

In one aspect, the lock member has a compact structure. This can preferably suppress the increase in the outer diameter of the housing pipe while allowing a structure in which the lock member is located in the housing pipe.

In one aspect, the lock member includes two of the engaging units, two of the engagement release units, and two of the arm units. The engaging unit, engagement release unit, and arm unit on a first side form a first movable unit. The engaging unit, engagement release unit, arm unit on a second side form a second movable unit. The two engaging units can be engaged with the shaft while holding the shaft from both sides of the shaft.

In one aspect, the engaging units are engaged with the shaft while holding the shaft from both sides of the shaft. This provides high engagement strength and allows the engagement of the engaging units with the shaft to be surely maintained unless the engagement release units are pressed inward.

In one aspect, the shaft includes a first engaging groove and a second engaging groove at positions at an interval in a longitudinal direction of an outer periphery of the shaft. The engaging unit of the first movable unit can be engaged with the first engaging groove on an engaging end of a front end of the engaging unit. The engaging unit of the second movable unit can be engaged with the second engaging groove on an engaging end of a front end of the engaging unit.

In one aspect the first engaging groove and second engaging groove provided on the shaft are engaged with the engaging units provided on the first and second movable units, respectively. This provides high engagement strength.

In one aspect, the engaging end of the first movable unit can be placed on a side opposite to the engagement release unit of the first movable unit based on the shaft. The engaging end of the second movable unit can be placed on a side opposite to the engagement release unit of the second movable unit based on the shaft.

In one aspect, the two engaging ends move in a direction away from the shaft with the inward displacement of the two engagement release units. Thus, only the inward displacement of the two engagement release units can surely and rapidly release the engagement of the pressure moving shaft and the lock member.

In one aspect, the housing pipe can be formed of a first member and a second member that have shapes separated horizontally in half. One of the first member and the second member can include a fixing unit to which the lock member is fitted. The lock member can have a shape open to the other side of the first member and the second member.

In one aspect, vertically layering the shaft, the lock member, the first member, and the second member with each other allows assembling of the trunk of the medical needle. This provides good assembly workability and thus contributes to an improvement in the productivity.

In one aspect, the lock member can be made of a material that is more deformable than the material of the housing pipe.

Certain embodiments described above can reduce the force of operation required for the release operation of the engagement of the lock member and the shaft, and thus can improve operability.

In one aspect, an operating unit to be operated by a user can be provided on a base end of the shaft. The operating unit can include elastically deformable and plate-like operating arms protruding in a front-end direction and extending so as to face the housing pipe. When being pressed toward the housing pipe side, the operating arms can press the engagement release units inward.

In one aspect, both the pressing operation to release the engagement of the lock member and the shaft and the pulling operation to move the shaft on the housing pipe in the base-end direction can continuously be performed as an operation on the operating unit. Because of this, good operability is provided. Furthermore, the operating arms have a plate-like shape. Appropriately increasing the lengths of the operating arms can readily reduce the force of the pressing operation required for the release of the engagement of the lock member and the shaft.

In one aspect, the medical needle can be formed as a winged needle including a wing shaft unit surrounding the first tube, and a pair of wings protruding from the wing shaft unit in directions opposite to each other.

In one aspect, the first tube can be narrowed. This can also narrow the wing shaft unit surrounding the first tube. The narrowed wing shaft unit stabilizes the needle tip of the needle body readily when the user picks the wing shaft unit through the base portions of the folded wings to insert the needle body into the living body. This can provide a medical needle with good operability.

According to the medical needle of certain embodiments of the present invention, narrowing the trunk can improve operability.

DETAILED DESCRIPTION

Hereinafter, the medical needle according to embodiments of the present invention will be described with reference to the appended drawings and with reference to a preferred embodiment.

Figure 1:
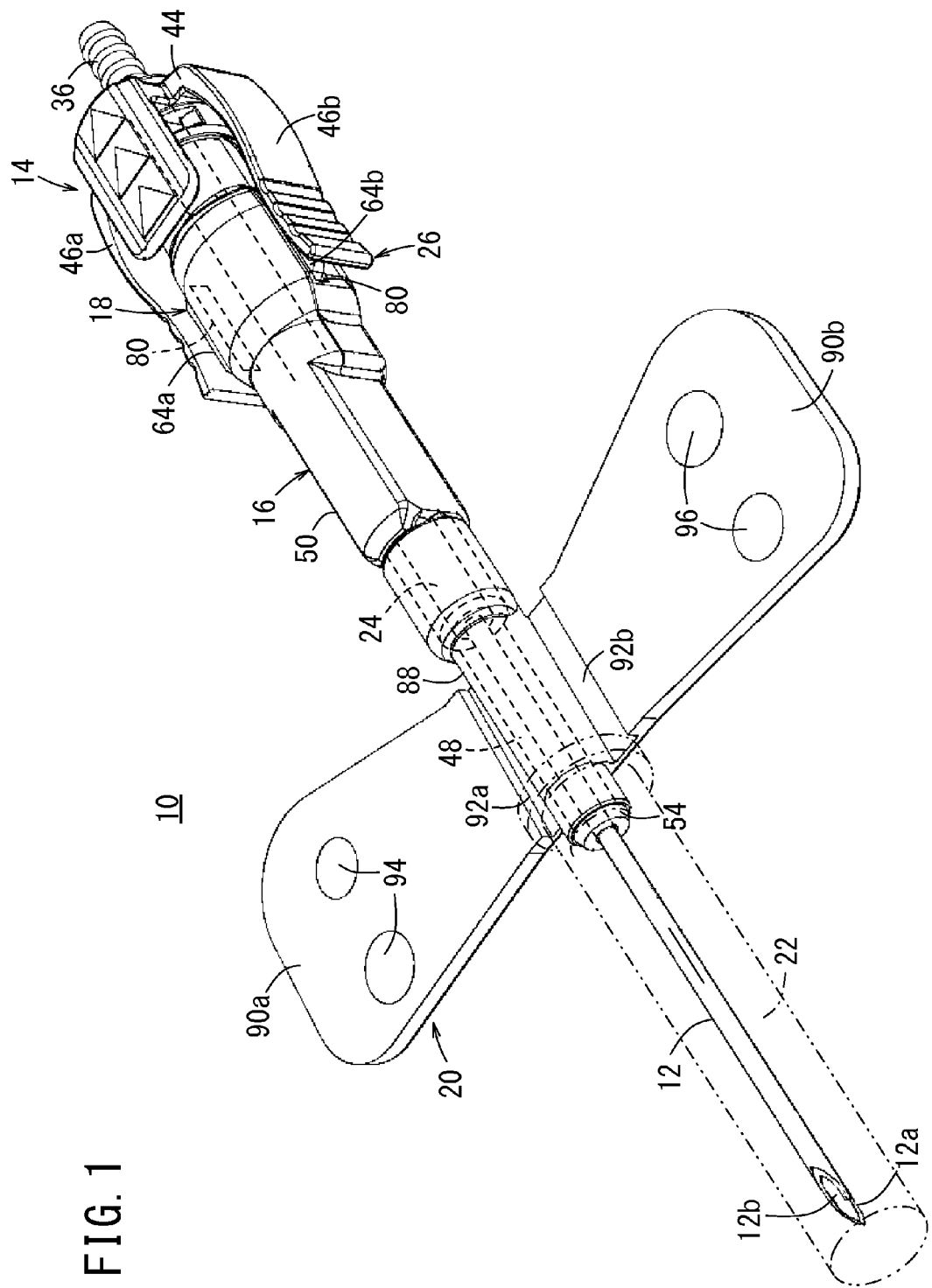
FIG. 1 is an overall perspective view of a medical needle according to a first embodiment of the present invention.
Figure 2:
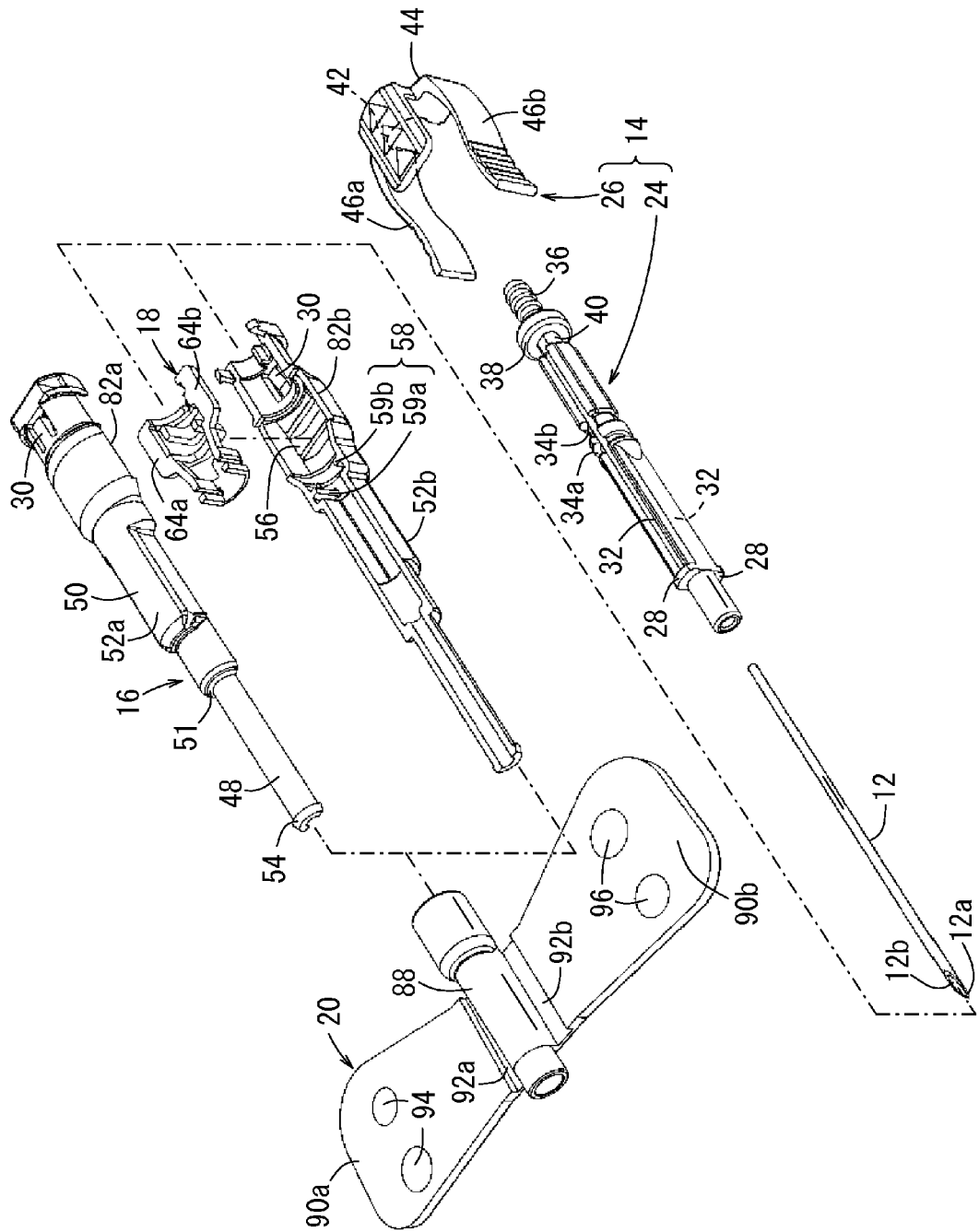
FIG. 2 is an exploded perspective view of the medical needle illustrated in FIG. 1.

FIG. 1 is an overall perspective view of the structure of a medical needle 10 according to an embodiment of the present invention. FIG. 2 is an exploded perspective view of the medical needle 10.

In the present embodiment, the medical needle 10 is a winged needle that is used, for example, for blood collection, blood transfusion, fluid infusion while being inserted into the patient's skin and fixed. Note that the present invention is not limited to the winged needle and can be applied to another types of medical needles 10, for example, to an indwelling needle used for a continuous intravenous infusion.

The medical needle 10 that is formed to be a winged needle includes a needle body 12, a hub 14, a housing pipe 16, a lock member 18, and a wing member 20.

The needle body 12 is a part to be inserted into the skin of the patient who receives a treatment such as blood collection, blood transfusion, or fluid infusion, and is made, for example, of stainless steel, aluminum, aluminum alloy, titanium, or titanium alloy. The sharp needle tip 12a is formed on the front end of the needle body 12. The needle body 12 has a circular pipe shape having a hollow portion acting as a flow channel, for example, for body fluid such as blood or infusion fluid. An opening 12b functioning as the inlet and outlet for fluid is formed on the front end of the needle body 12.

A cap 22 is attached to the medical needle 10 before the medical needle 10 is used. The cap 22 has a pipe shape with a hollow capable of housing the needle body 12 therein. The cap 22 is fitted to the front-end side of the wing member 20 at the base end so as to be attachable to the medical needle 10 while covering the needle body 12. When the medical needle 10 is used, pulling the cap 22 in the front-end direction can remove the cap 22 from the wing member 20 and expose the needle body 12.

The hub 14 is connected to the base end of the needle body 12 to support the needle body 12. In the present embodiment, the hub 14 includes a shaft 24 and an operating unit 26. The shaft 24 has a hollow portion which is coaxially connected to the base end of the needle body 12. The hollow portion is communicated with the inner cavity of the needle body 12. The operating unit 26 is fixed near the base end of the shaft 24. The base end of the needle body 12 is inserted and fixed in the front end of the shaft 24. The shaft 24 has a larger diameter than the needle body 12.

Figure 7:
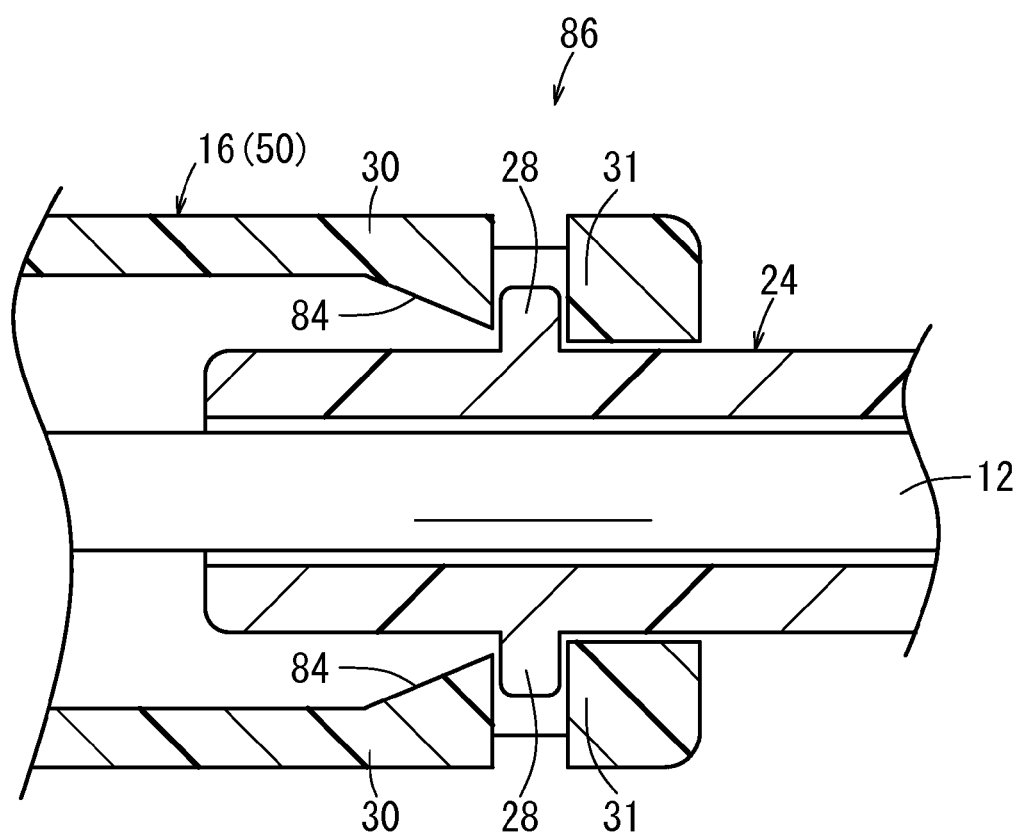
FIG. 7 is a cross-sectional view of the structure in which the shaft is engaged with the housing pipe and the peripheral portions thereof, in the medical needle in the state illustrated in FIG. 5.

Protrusions 28 protruding in a direction perpendicular to the axis line (for example, protruding in a vertical direction in the example illustrated in FIG. 7) are provided on parts in a circumferential direction near the front end of the shaft 24 (a position slightly nearer to the base-end side than the front end). The protrusions 28 are portions that are engaged with elastic engaging portions 30 provided on the housing pipe 16 when the shaft 24 moves to a backward position (a second position described below) on the housing pipe 16. Note that, instead of the two protrusions 28, an annular protrusion extending in a circumferential direction can be provided. Alternatively, the protrusions 28 or the annular protrusion can be provided on the front end of the shaft 24 instead of near the front end of the shaft 24.

A guide groove 32 is provided on each of the upper portion and lower portion of the shaft 24 along the longitudinal direction of the shaft 24. The guide groove 32 has a length approximately corresponding to the range in which the shaft 24 can slide on the housing pipe 16.

Figure 3:
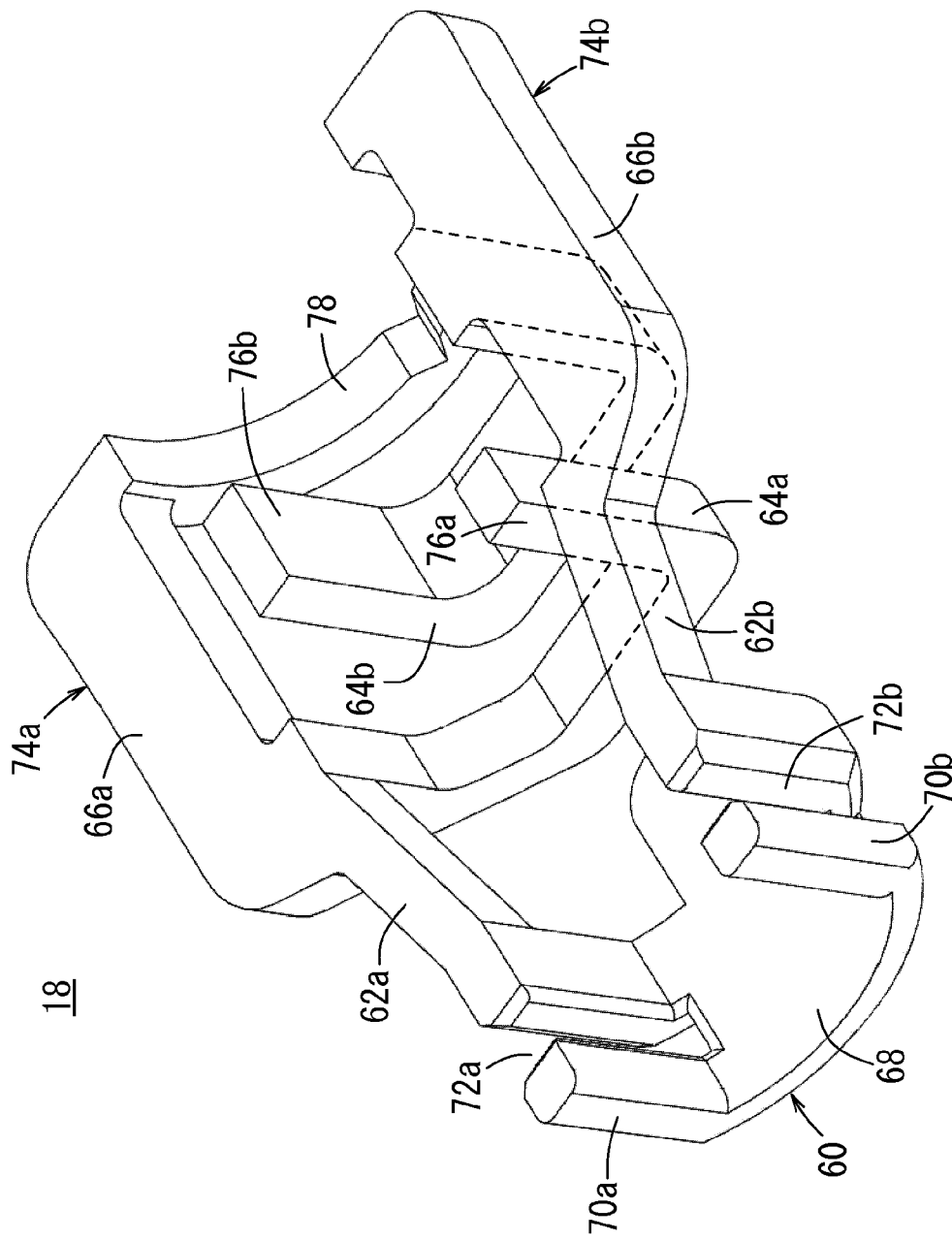
FIG. 3 is a perspective view of a lock member.
Figure 4:
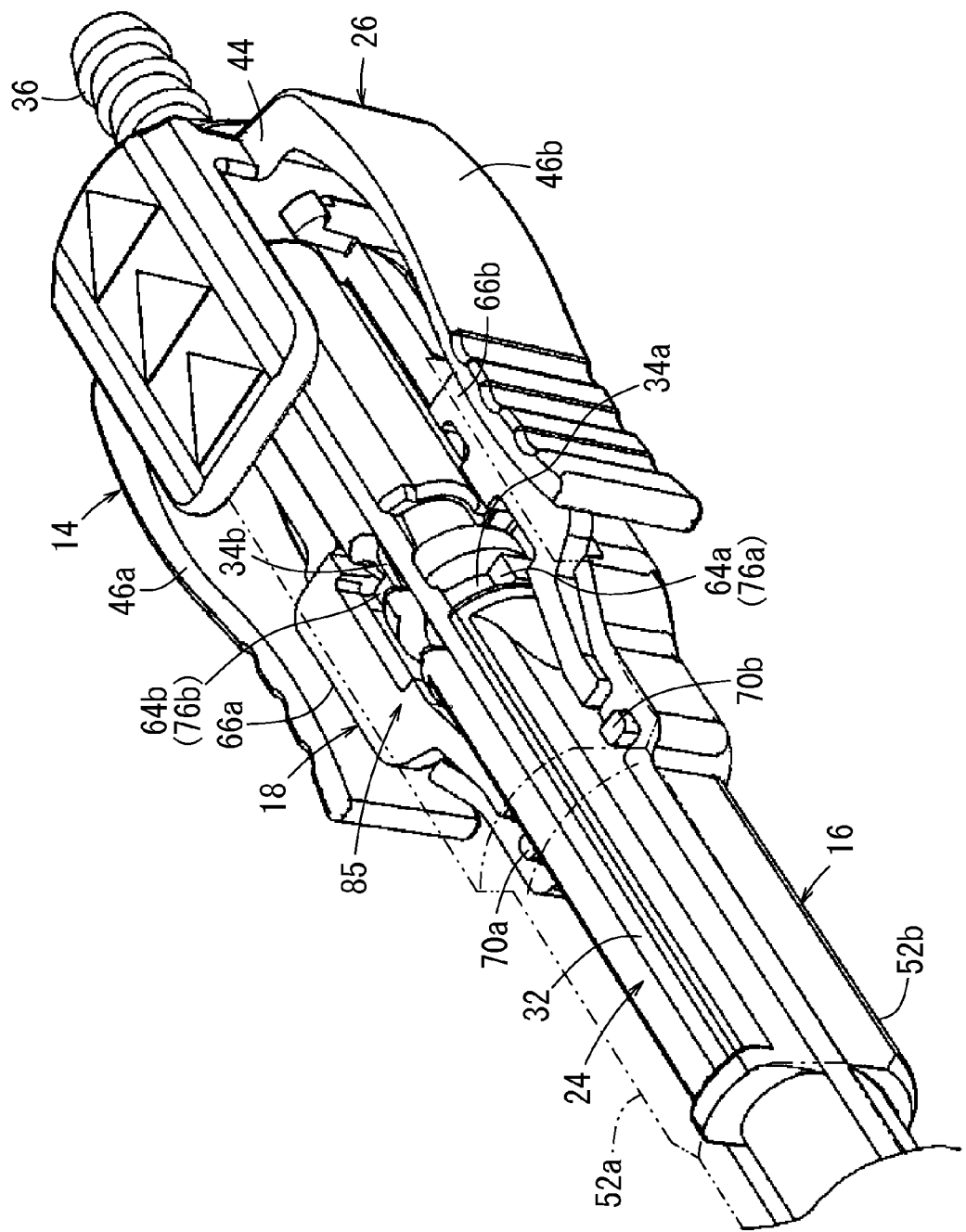
FIG. 4 is a perspective view of the engagement of the lock member and a shaft.

As illustrated in FIG. 4, two engaging grooves 34a and 34b are provided on the outer periphery of the longitudinal intermediate portion of the shaft 24 (near the longitudinal center in the example illustrated in the drawing). The two engaging grooves 34a and 34b are provided at positions at an interval in the longitudinal direction of the shaft 24, and extend in a circumferential direction. The engaging grooves 34a and 34b in the illustrated example are formed in a range to cross the guide groove 32 and make the circuit of the shaft 24. However, the engaging grooves 34a and 34b can be formed in a circumferential range necessary and sufficient to be engaged with the engaging ends 76a and 76b of the lock member 18 (see FIG. 3). Thus, the engaging grooves 34a and 34b can be provided only at places facing the engaging ends 76a and 76b of the lock member 18 in the shaft 24. A tube connecting unit 36 connectable to a tube (not illustrated in the drawings) connected, for example, to a fluid infusion bag or a blood bag is provided on the base end of the shaft 24.

A flange 38 bulging in a radial direction is provided nearer to the front-end side than to the tube connecting unit 36 and near the base end of the shaft 24. A reduced radius unit 40 that is narrower than the parts therearound is provided between the guide groove 32 and the flange 38 in the shaft 24. Fitting the operating unit 26 to the reduced radius unit 40 fixes the shaft 24 and the operating unit 26 to each other.

The operating unit 26 is a part that the user holds with the fingers for a pressing operation or a moving back operation. The operating unit 26 includes a base unit 44 on which a fitting groove 42 that is a notch fitted to the reduced radius unit 40 is formed, and a pair of operating arms 46a and 46b that extend from the outer ends of the base unit 44 (both of right and left ends in the illustrated example) in the front-end direction and that are elastically deformable in a radial direction of the shaft 24 (the horizontal direction in the illustrated example). Each of the operating arms 46a and 46b is a plate-like portion that separates from the outer periphery of the housing pipe 16 and extends so as to face the outer periphery, and that is elastically deformable inward (in a direction in which the pair of operating arms 46a and 46b approach each other) when the user holds the operating arms and presses them from the outside.

Each of the operating arms 46a and 46b is provided with a skid-prevention groove on the outer surface of the front end. The inner surfaces of the operating arms 46a and 46b near the front end face the engagement release units 66a and 66b of the lock member 18, respectively. In an operation for releasing the engagement of the lock member 18 and the shaft 24 (the engagement release operation), the operating arms 46a and 46b are pressed inward. The force for the pressing operation required in the engagement release operation relates, for example, to the material, thickness, width, or length of each of the operating arms 46a and 46b. Thus, the material, thickness, width, length, and the like of each of the operating arms 46a and 46b are preferably set such that pressing the operating arms 46a and 46b with a small amount of force of operation can release the engagement of the lock member 18 and the shaft 24.

The materials of the shaft 24 and the operating unit 26 are not especially limited. However, examples include polyvinyl chloride, polyethylene, polypropylene, cyclic polyolefin, polystyrene, poly-(4-methylpentene-1), polycarbonate, acrylate resin, acrylonitrile-butadiene-styrene copolymer, polyethylene terephthalate, polyester such as polyethylene naphthalate, butadiene-styrene copolymer, or polyamide (e.g., nylon 6, nylon 6,6, nylon 6,10, or nylon 12).

Figure 5:
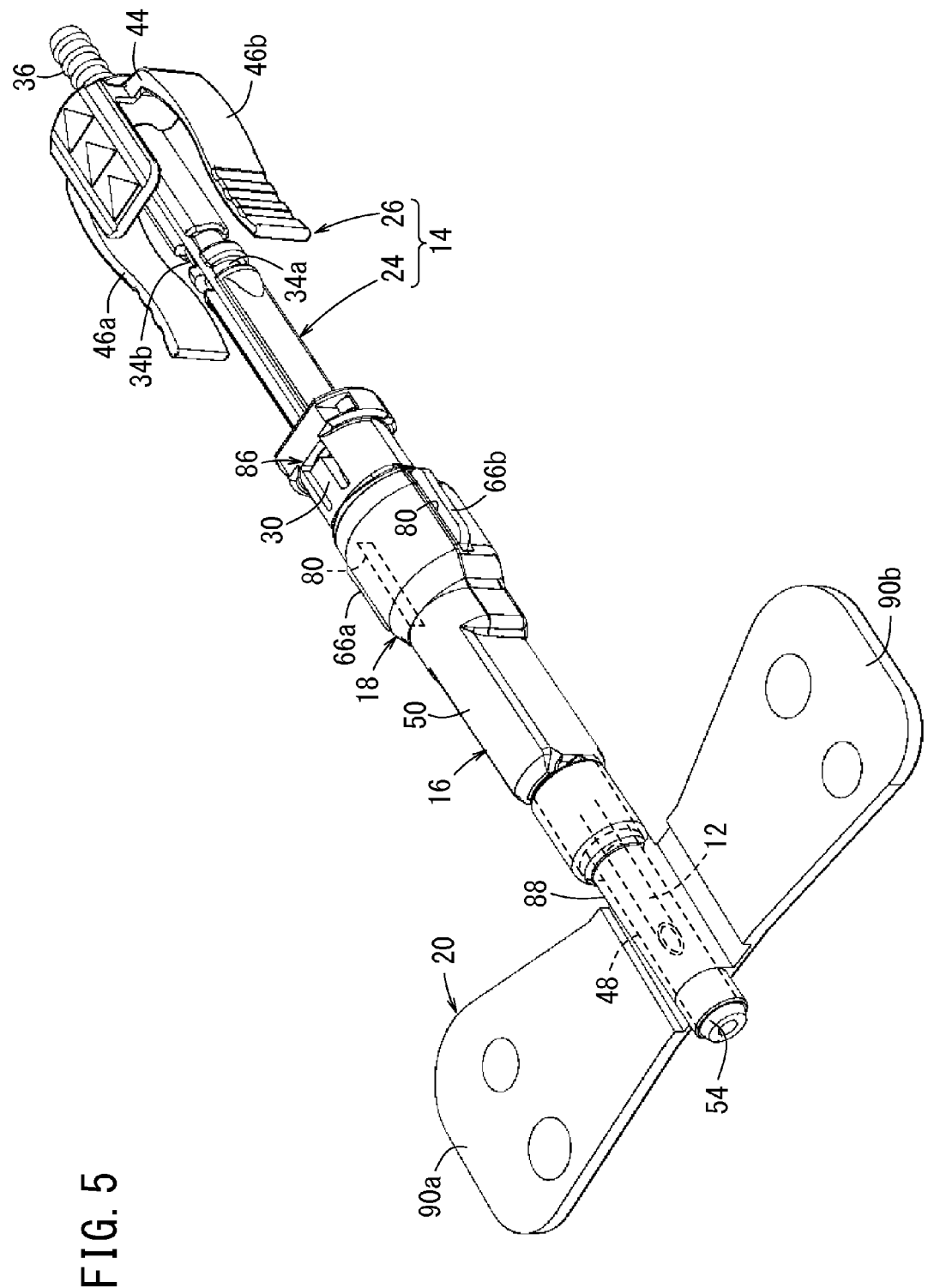
FIG. 5 is an overall perspective view of the medical needle of which needle body is housed in a housing pipe.

As illustrated in FIGS. 1 and 2, the housing pipe 16 includes a first tube 48 forming the front-end side, and a second tube 50 that is provided on the base end of the first tube 48, is thicker (has a larger diameter) than the first tube 48, and in which the shaft 24 is displaceably placed in the axial direction. As illustrated in FIG. 5, the housing pipe 16 is configured to cover the needle tip 12a of the needle body 12 when the shaft 24 is moved back to a predetermined position on the housing pipe 16. In other words, the housing pipe 16 functions as a protector covering the needle tip 12a of the needle body 12 after the medical needle 10 is used.

The housing pipe 16 is fitted to the inside of the wing shaft unit 88 in the wing member 20 in a predetermined range near the front end. As illustrated in FIG. 2, in the present embodiment, the housing pipe 16 includes the first member 52a and the second member 52b that have shapes separated horizontally in half. Coupling the first member 52a with the second member 52b forms an inner cavity that penetrates in the axial direction such that the needle body 12 can be inserted therein.

The first tube 48 is a relatively narrow part placed in the wing shaft unit 88. The circular guard 54 bulging outward in a radial direction is provided on the front end of the first tube 48. The circular guard 54 and a step 51 (see FIG. 2) between the first tube 48 and the second tube 50 determines the position of the housing pipe 16 in relative to the wing shaft unit 88 in the axial direction. A spline structure (not illustrated in the drawings) prevents the housing pipe 16 and the wing shaft unit 88 from relatively rotating.

The second tube 50 is thicker (has a larger diameter) than the first tube 48. The shaft 24 is placed inside the second tube 50 displaceably in the axial direction. The shaft 24 can slide on the housing pipe 16 from a first position at which the front end of the needle body 12 protrudes from the housing pipe 16 by a predetermined length and the front end of the shaft 24 is placed in the second tube 50 (see FIG. 1) to a second position at which the front end of the needle body 12 is housed in the housing pipe 16 (see FIG. 5).

As illustrated in FIG. 2, a placement unit 56 configured to place (house) the lock member 18 is provided at the intermediate portion of the second tube 50 in the axial direction. The placement unit 56 has a larger diameter than the portion around the placement unit 56 in order to place the lock member 18 therein. The placement unit 56 is provided with a fixing unit 58 to fix the lock member 18 in the axial direction. The fixing unit 58 in the illustrated example includes ribs 59a and 59b protruding inward from the tube wall forming the second tube 50. The ribs 59a and 59b are provided at the positions facing each other and having the axis line of the second tube 50 therebetween.

As illustrated in FIGS. 3 and 4, the lock member 18 includes a base unit 60 seized and fixed on the inner surface of the housing pipe 16, arm units 62a and 62b that extend from the base unit 60 and are elastically deformable in the radial direction of the housing pipe 16 (the horizontal direction in the drawing), engaging units 64a and 64b releasably engaged with the shaft 24, and engagement release units 66a and 66b protruding to the outside of the housing pipe 16 through side holes 80 provided on the housing pipe 16. The lock member 18 is open to the first member 52a side. The engaging unit 64a and engagement release unit 66a on a side are provided at the arm unit 62a on one side. The engaging unit 64b and engagement release unit 66b on the other side is provided at the arm unit 62b on the other side.

The base unit 60 includes a bottom 68, and side portions 70a and 70b extending upward from both of right and left sides of the bottom 68. The base unit 60 is curved into an approximate U shape so as to have a convex shape downward (to the second member 52b side). Slits 72a and 72b configured to be fitted to the rib-shaped fixing units 58 provided on the housing pipe 16, respectively, are formed on the side portions 70a and 70b. Fitting the fixing units 58 to the side portions 70a and 70b seizes the lock member 18 on the housing pipe 16 in the axial direction. The arm unit 62a, engaging unit 64a, and engagement release unit 66a on one side form a first movable unit 74a. The arm unit 62b, engaging unit 64b, and engagement release unit 66b on the other side form a second movable unit 74b.

The arm unit 62a and engagement release unit 66a of the first movable unit 74a and the arm unit 62b and engagement release unit 66b of the second movable unit 74b are placed so as to face each other while having the axis line of the housing pipe 16 therebetween. The engaging unit 64a of the first movable unit 74a and the engaging unit 64b of the second movable unit 74b are placed at an interval in the axial direction of the housing pipe 16.

The engaging unit 64a of the first movable unit 74a is curved into an approximate U shape such that the engaging end 76a on the front end is engaged with the engaging groove 34a provided on the shaft 24 and the other portions of the engaging unit 64a do not contact or are not engaged with the shaft 24. Specifically, the engaging unit 64a is curved so as to have a convex shape downward (to the second member 52b side). When the shaft 24 is placed at the first position, the engaging end 76a of the first movable unit 74a is placed on a side opposite to the engagement release unit 66a based on the shaft 24.

The arm unit 62b of the second movable unit 74b has a curved shape such that the engaging end 76b on the front end is engaged with the other engaging groove 34b provided on the shaft 24 and the other portions of the arm unit 62b do not contact or are not engaged with the shaft 24. Specifically, the engaging unit 64b is curved so as to have a convex shape downward (the second member 52b side). When the shaft 24 is placed at the first position, the engaging end of the second movable unit 74b is placed on a side opposite to the engagement release unit 66b based on the shaft 24.

When the shaft 24 is placed at the first position (see FIG. 1), the engaging end 76a of the first movable unit 74a and the engaging end 76b of the second movable unit 74b are opposite to each other based on the shaft 24. A connecting portion 78 that extends between the two engagement release units 66a and 66b and is elastically deformable is further provided at the lock member 18. The connecting portion 78 is curved so as to have a convex shape downward (to the second member 52b side).

When the shaft 24 is placed at the first position on the housing pipe 16 and the engaging units 64a and 64b of the lock member 18 are engaged with the engaging grooves 34a and 34b of the shaft 24, the motion of the shaft 24 on the housing pipe 16 in the axial direction is prevented. On the other hand, when separating the engaging end from the engaging grooves 34a and 34b at a predetermined distance or more releases the engagement of the engaging units 64a and 64b and the engaging grooves 34a and 34b, the motion of the shaft 24 on the housing pipe 16 in the axial direction is allowed. In other words, in the present embodiment, the engaging units 64a and 64b of the lock member 18 and the engaging grooves 34a and 34b of the shaft 24 form a first lock unit 85 (see FIG. 4) configured to releasably seize the shaft 24 at the first position on the housing pipe 16.

As illustrated in FIG. 5, side holes 80 that extend in the axial direction of the housing pipe 16 and each have a long hole shape are provided on both the right and left sides of the housing pipe 16. The engagement release units 66a and 66b of the lock member 18 protrude to the outside of the housing pipe 16 through the side holes 80. The side holes 80 are formed of a notched concave 82a (see FIG. 2) provided on the first member 52a and a notched concave 82b (see FIG. 2) provided on the second member 52b.

As illustrated in FIGS. 2 and 7, the elastic engaging portions 30 are provided at the positions facing each other near the base end of the housing pipe 16. Specifically, one of the elastic engaging portions 30 is provided on the first member 52a while the other elastic engaging portion 30 is provided on the second member 52b. Each of the elastic engaging portions 30 includes a tapered surface 84 inclined toward the inside of the housing pipe 16 in the base-end direction in the housing pipe 16. When the shaft 24 moves from the first position to the second position on the housing pipe 16, the elastic engaging portions 30 are elastically deformed outward by the protrusions 28 provided on the shaft 24 pressing the elastic engaging portions 30 outward. This causes the protrusions 28 to cross over the elastic engaging portions 30.

When the shaft 24 is placed at the second position at which the shaft 24 is displaced nearest to the base end side on the housing pipe 16, the motion of the shaft 24 between the elastic engaging portions 30 and the wall portions 31 facing the elastic engaging portions 30 in the axial direction on the housing pipe 16 is prevented. In the present embodiment, the elastic engaging portions 30, the wall portions 31, and the protrusions 28 form a second lock unit 86 configured to actually unreleasably hold the shaft 24 at the second position on the housing pipe 16.

The materials of the housing pipe 16 and the lock member 18 are not especially limited. For example, one or more materials selected from the materials cited as the exemplary materials of the shaft 24 and the operating unit 26 above can be used. When the lock member 18 is made of a material more easily deformed than the housing pipe 16, namely, a soft material (e.g., polyacetal), the arm units 62a and 62b of the lock member 18 are elastically deformed easily with a small amount of force. This can reduce the force of the pressing operation to the operating arms 46a and 46b and improve operability when the engagement of the lock member 18 and the shaft 24 is released.

As illustrated in FIG. 1, the wing member 20 includes a wing shaft unit 88 having a hollow portion therein, and a pair of wings 90a and 90b horizontally protruding from the wing shaft unit 88. The wings 90a and 90b are connected to the wing shaft unit 88 at the base portions, and each has a plate-like shape of which width increases outward from the base portion. The wings 90a and 90b are flexible such that bending or curving the portions near the base portions can open or close the wings. Thin portions 92a and 92b are formed at the portions near the base portions of the wings 90a and 90b along the axial direction of the wing shaft unit 88 in order to facilitate the opening and closing.

A plurality of (two in the illustrated example) convexities 94 is provided on the upper surface of one of the wing 90a while a plurality of (two in the illustrated example) concavities 96 (as many as the convexities 94) is provided on the upper surface of the other wing 90b. When the pair of wings 90a and 90b is closed (folded), the convexities 94 are fitted to the concavities 96. A single convexity 94 and a single concavity 96 can be provided.

The wing shaft unit 88 and wings 90a and 90b in the illustrated example are integrally formed. However, the wing shaft unit 88 and the wings 90a and 90b can separately be formed and then can be coupled with each other to form the wing member 20. The materials of the wing shaft unit 88 and the wings 90a and 90b are not especially limited. For example, one or more kinds of materials selected from the materials cited as the exemplary materials of the housing unit or the like can be used.

The wing shaft unit 88 is made of a rigid material so as not to bend in use while the wings 90a and 90b can be made of a soft material so as to have an appropriate flexibility with which the base portions are easily bent such that the wings can be opened and closed. The wing member 20 in which the wing shaft unit 88 and the wings 90a and 90b are integrally formed can be produced by bicolor molding, for example, using a resin material with a relatively high rigidity and a resin material with a relatively low rigidity.

The medical needle 10 according to the present embodiment basically has the structure described above. Hereinafter, the function and effect will be described.

In, for example, blood collection, blood transfusion, or fluid infusion using the medical needle 10 having the structure described above, the cap 22 is first removed from the medical needle 10 to expose the needle body 12. Next, the user picks the pair of wings 90a and 90b with the fingers to close (fold) the wings. Specifically, the wings are closed while the base portions of both the wings 90a and 90b are bent and the wing 90a on one side overlaps with the wing 90b on the other side. At that time, the convexity 94 provided on the wing 90a is fitted to the concavity 96 provided on the other wing 90b so as to be prevented from being misaligned with each other.

After closing the wings 90a and 90b, the user inserts the needle body 12 into the living body while holding the closed wings 90a and 90b with the fingers. At this time, as illustrated in FIG. 4, because the engaging units 64a and 64b of the lock member 18 are engaged with the engaging grooves 34a and 34b provided on the shaft 24, the motion of the shaft 24 in the axial direction on the housing pipe 16 is prevented. In other words, the needle body 12 is prevented from moving back relative to the housing pipe 16 and the wing member 20 fixed thereon. Therefore, the needle body 12 is prevented from moving back on the housing pipe 16 due to the resistance generated when the user holds the wing member 20 with the fingers and inserts the needle body 12 into the living body.

To keep the needle body 12 inserted in the living body, the wings 90a and 90b are returned to the open position and fixed on the skin, for example, with adhesive tape.

After the completion of the blood collection, blood transfusion, fluid infusion, or the like, the fixation of the wings 90a and 90b on the skin with adhesive tape is released and the needle body 12 is removed from the living body. After the completion of use of the medical needle 10 as described above, a "storage operation" to cover and store the needle body 12 with the housing pipe 16 functioning as a protector is performed in order to prevent a health-care professional, for example, who disposes of the medical needle 10 from carelessly touching the needle body 12.

As the first step of the storage operation, the engagement of the engaging units 64a and 64b with the engaging grooves 34a and 34b is released such that the shaft 24 can move in the base-end direction on the housing pipe 16. Specifically, the two operating arms 46a and 46b of the operating unit 26 are pressed inward (to the housing pipe 16 side). Pressing the operating arms 46a and 46b inward presses the engagement release units 66a and 66b of the lock member 18 that face the insides of the operating arms inward with the pressed operating arms 46a and 46b. This causes the elastic deformation of the arm units 62a and 62b, thereby displacing the engagement release units 66a and 66b toward the shaft 24 side. With the displacement of the engagement release units 66a and 66b, the engaging units 64a and 64b corresponding to the engagement release units are integrally displaced with the engagement release units 66a and 66b. This displaces the engaging ends 76a and 76b in a direction away from the shaft 24, leading to the release of the engagement of the engaging units 64a and 64b with the engaging grooves 34a and 34b.

Figure 6:
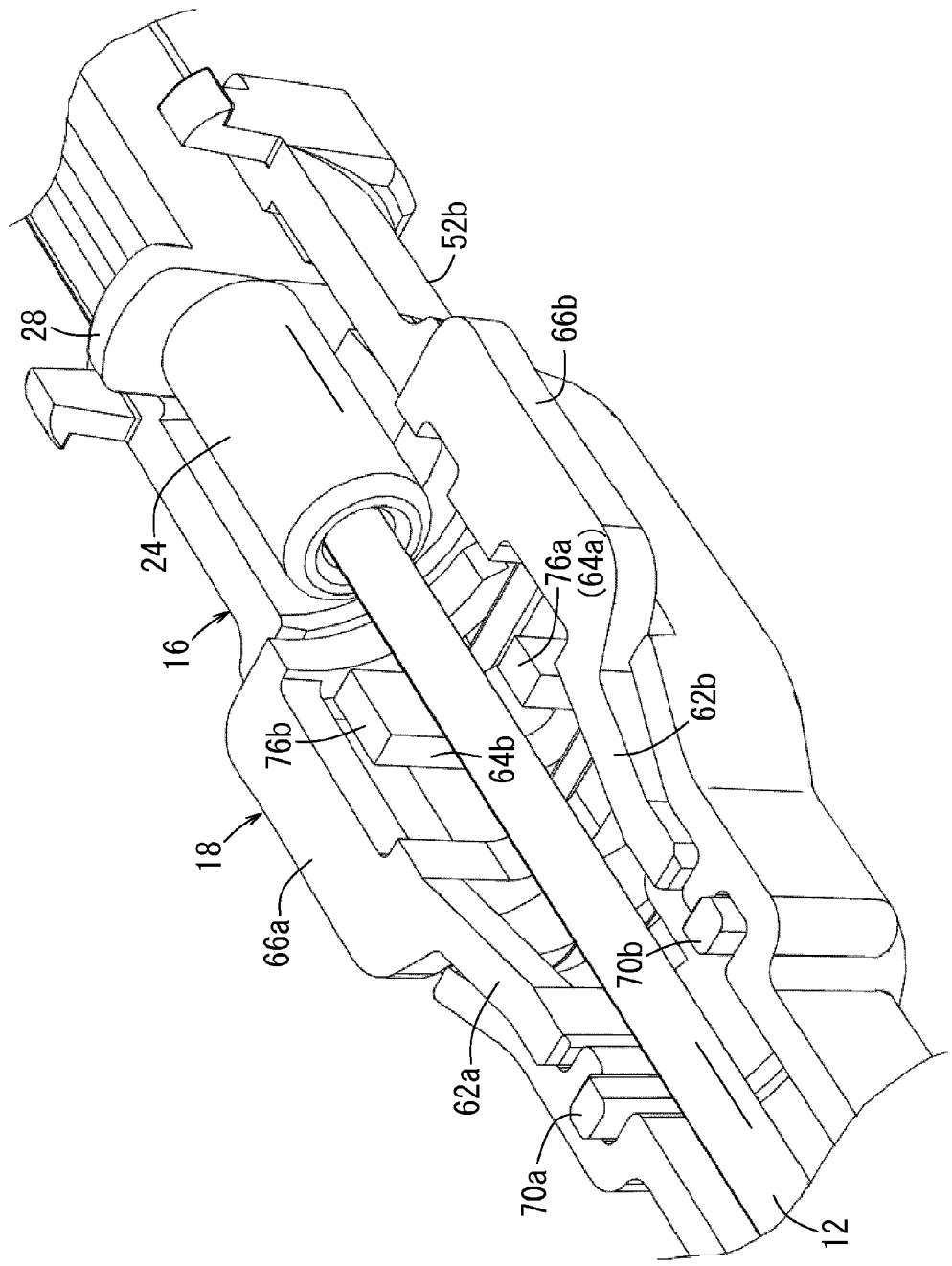
FIG. 6 a perspective view of the lock member and the peripheral portions in the medical needle in the state illustrated in FIG. 5.

Next, as the second step of the storage operation, the operating unit 26 is pulled relative to the housing pipe 16 in the base-end direction while the operating arms 46a and 46b are kept pressed inward, in other words, the engagement of the engaging units 64a and 64b with the engaging grooves 34a and 34b is kept released. Accordingly, the needle body 12 fixed on the front end of the hub 14 is displaced relative to the housing pipe 16 in the base-end direction. When the hub 14 is moved nearest to the base-end side on the housing pipe 16, the needle body 12 is positioned inside of the housing body (specifically, the inside of the first tube 48). As illustrated in FIGS. 5 and 6, when the shaft 24 is moved to a predetermined backward position (the second position), the function of the second lock unit 86 described above prevents the shaft 24 from moving forward on the housing pipe 16 (see FIG. 7). Thus, the needle body 12 does not protrude from the front end of the housing pipe 16 again. The function of the second lock unit 86 also prevents the shaft 24 from moving backward on the housing pipe 16. Therefore, the needle body 12 is efficiently prevented from being removed from the base end of the housing pipe 16.

As described above, according to the medical needle 10 of certain embodiments the present invention, because the front end of the shaft 24 is placed nearer to the base-end side than to the first tube 48 of the housing pipe 16 in the second tube 50 when the shaft 24 is placed nearest to the front-end side in the range of motion, it is easy to form the first tube 48 of the housing pipe 16 to be narrowed. In other words, because the shaft 24 is not inserted in the first tube 48 forming the front-end side of the housing pipe 16, the outer diameter of the first tube 48 can be reduced. This allows the trunk of the medical needle 10 to be easily narrowed. The user easily holds the narrowed trunk with the fingers. This can provide a medical needle 10 with good operability.

Furthermore, in certain embodiments of the present invention, a structure in which the lock member 18 is placed not on the base end of the housing pipe 16 but nearer to the front-end side than to the base end is adopted. This prevents the entire length of the medical needle 10 from increasing in spite of the structure in which the front end of the shaft 24 is placed nearer to the base-end side in comparison with a conventional technique. As described above, the medical needle 10 according to certain embodiments of the present invention can improve the operability by narrowing the trunk without increasing the entire length.

In the present embodiment, the lock member 18 includes the base unit 60, the arm units 62*a* and 62*b*, the engaging units 64*a* and 64*b*, and the engagement release units 66*a* and 66*b*. When the engagement release units 66*a* and 66*b* are pressed inward, the engaging units 64*a* and 64*b* are displaced in a direction away from the shaft 24. This releases the engagement of the engaging units 64*a* and 64*b* with the shaft 24. The lock member 18 described above can have a compact structure. This can preferably suppress the increase in the outer diameter of the housing pipe 16 while adopting the structure in which the lock member 18 is placed in the housing pipe 16.

In the present embodiment, the lock member 18 is provided in the housing pipe 16. In the structure described above, even when the shaft 24 is moved backward, the lock member 18 is not exposed and thus does not interrupt the operation.

In the present embodiment, the lock member 18 includes the two engaging units 64*a* and 64*b*, the two engagement release units 66*a* and 66*b*, and the two arm units 62*a* and 62*b*. The engaging unit 64*a*, engagement release unit 66*a*, and arm unit 62*a* on one side form the first movable unit 74*a*. The engaging unit 64*b*, engagement release unit 66*b*, and arm unit 62*b* on the other side form the second movable unit 74*b*. The two engaging units 64*a* and 64*b* are engaged with the shaft 24 while holding the shaft 24 from both sides of the shaft 24. As described above, the engaging units 64*a* and 64*b* are engaged with the shaft 24 while holding the shaft 24 from both sides of the shaft 24. This provides high engagement strength and allows the engagement of the engaging units 64*a* and 64*b* with the shaft 24 to be surely maintained unless the engagement release units 66*a* and 66*b* are pressed inward.

In the present embodiment, the housing pipe 16 is formed of the first member 52*a* and the second member 52*b* that have shapes separated horizontally in half. The base unit 60 is fitted to the fixing unit 58 provided on the first member 52*a*. The lock member 18 has a shape open to the second member 52*b* side. In the structure described above, sequentially layering the first member 52*a*, the lock member 18, the shaft 24, and the second member 52*b* with each other allows assembling the trunk of the medical needle 10. This provides good assembly workability and thus contributes to an improvement in productivity. Therefore, the structure has good assembly workability and contributes to an improvement in productivity.

Note that, although being provided on the first member 52*a* in the present embodiment, the placement unit 56 of the lock member 18 can be provided on the second member 52*b* side as an exemplary variation. In such a case, the lock member 18 is placed upside down from the position illustrated in FIG. 1. Alternatively, as an exemplary variation, the lock member can be placed back to front from the position illustrated in FIG. 1.

In the present embodiment, because the lock member 18 is made of a material more deformable than the housing pipe 16, the force of operation required for the release operation of the engagement of the lock member 18 and the shaft 24 can be reduced, and thus the operability can be improved.

In the present embodiment, both of the pressing operation to release the engagement of the lock member 18 and the shaft 24 and the pulling operation to move the shaft 24 in the base-end direction on the housing pipe 16 can continuously be performed as an operation on the operating unit 26. This provides good operability. Furthermore, the operating arms 46*a* and 46*b* have a plate-like shape. Appropriately increasing the lengths of the operating arms 46*a* and 46*b* can readily reduce the force of the pressing operation required for the release of the engagement of the lock member 18 and the shaft 24.

In the present embodiment, the medical needle 10 is formed as a winged needle including the wing shaft unit 88 and the pair of wings 90*a* and 90*b*. As described above, because the first tube 48 can be narrowed, the wing shaft unit 88 surrounding the first tube 48 can also be narrowed. The narrowed wing shaft unit 88 stabilizes the needle tip 12*a* of the needle body 12 readily when the user picks the wing shaft unit 88 through the base portions of the folded wings 90*a* and 90*b* to insert the needle body 12 into the living body. Therefore, a winged needle with good operability can be provided.

The present invention has been described above with citation of the preferable embodiment. However, the present invention is not limited to the embodiment. It is obvious that the present invention can be variously changed without departing from the scope of the invention.

What is claimed is:

1. A medical needle comprising:
   a needle body including a needle tip on a front end of the needle body;
   a shaft provided on a base end of the needle body;
   a housing pipe including a first tube, and a second tube that is provided on a base end of the first tube, the shaft being located in the housing pipe such that the shaft is displaceable in an axial direction relative to the housing pipe; and
   a lock member that includes:
     a base unit fixed on an inner surface of the housing pipe,
     at least one elastically deformable arm unit protruding in a base end direction from the base unit,
     at least one engaging unit that extends from the at least one arm unit at a first radial side of the shaft, is curved so as to extend around the shaft, and is releasably engaged with the shaft at a second radial side of the shaft, and
     at least one engagement release unit that extends from the at least one arm unit and protrudes to an outside of the housing pipe through at least one side hole of the housing pipe, the lock member being fixed in the housing pipe,
   wherein the shaft is slidable in the housing pipe from (i) a first position at which the front end of the needle body protrudes from the housing pipe by a predetermined length and the front end of the shaft is located in the second tube to (ii) a second position at which the front end of the needle body is located in the housing pipe, wherein, when the at least one engaging unit is engaged with the shaft, the shaft is held at the first position in the housing pipe, and wherein, when the at least one engagement release unit is pressed inward, displacement of the at least one engaging unit in a direction away from the shaft releases the engagement of the at least one engaging unit with the shaft.

2. The medical needle according to claim 1,
wherein the lock member includes two of the engaging units, two of the engagement release units, and two of the arm units,
wherein a first engaging unit, a first engagement release unit, and a first arm unit, located on a first side, form a first movable unit,
wherein a second engaging unit, a second engagement release unit, and a second arm unit, located on a second side, form a second movable unit, and
wherein the two engaging units are engaged with the shaft while holding the shaft from two opposing sides of the shaft.

3. The medical needle according to claim 2,
wherein the shaft includes a first engaging groove and a second engaging groove at positions intervaled in a longitudinal direction of an outer periphery of the shaft,
wherein the first engaging unit of the first movable unit is engaged with the first engaging groove on a first engaging end of the first engaging unit, and
wherein the second engaging unit of the second movable unit is engaged with the second engaging groove on a second engaging end of the second engaging unit.

4. The medical needle according to claim 3,
wherein the first engaging end of the first movable unit is located on a side of the shaft that is opposite to the first engagement release unit of the first movable unit, and
wherein the second engaging end of the second movable unit is located on a side of the shaft that is opposite to the second engagement release unit of the second movable unit.

5. The medical needle according to claim 1,
wherein the housing pipe includes a first member and a second member each forming a half of the housing pipe,
wherein one of the first member and the second member includes a fixing unit to which the lock member is fitted, and the lock member has a shape open to the other of the first member and the second member.

6. The medical needle according to claim 1, wherein the lock member is made of a material that is more deformable than a material of the housing pipe.

7. The medical needle according to claim 1,
wherein an operating unit configured to be operated by a user is provided on a base end of the shaft,
wherein the operating unit includes elastically deformable and plate-like operating arms protruding in a front-end direction and extending so as to face the housing pipe, and
wherein, when pressed toward the housing pipe, the operating arms press the engagement release units inward.

8. The medical needle according to claim 1, further comprising:
a wing shaft unit surrounding the first tube, and
a pair of wings protruding from the wing shaft unit in directions opposite to each other.

9. The medical needle according to claim 1,
wherein the shaft includes at least one protrusion protruding in a direction perpendicular to the axial direction,
wherein the housing pipe includes at least one engaging portion, and
wherein the at least one protrusion of the shaft is configured to engage with the at least one engaging portion of the housing pipe when the shaft is in the second position.

10. The medical needle according to claim 7,
wherein the shaft includes a flange, and a reduced diameter unit located on a front end side of the flange, and
wherein the operating unit is fitted to the reduced diameter unit to fix the shaft to the operating unit.

11. The medical needle according to claim 1, wherein a diameter of the second tube is larger than a diameter of the first tube.

12. The medical needle according to claim 5, wherein the fixing unit includes at least one rib protruding inwardly from a wall of the second tube.

13. The medical needle according to claim 1, wherein the at least one engaging unit is U-shaped.

14. The medical needle according to claim 5, wherein the at least one side hole is formed of a first notched concave section of the first member, and a second notched concave section of the second member.

15. The medical needle according to claim 8, wherein the wings are foldable.

16. The medical needle according to claim 15, wherein a first one of the wings includes at least one convexity, and a second one of the wings includes at least one concavity, such that, when the wings are folded, the at least one convexity is fitted to the at least one concavity.

17. A method comprising:
providing a medical needle comprising:
a needle body including a needle tip on a front end of the needle body;
a shaft provided on a base end of the needle body;
a housing pipe including a first tube, and a second tube that is provided on a base end of the first tube, the shaft being located in the housing pipe such that the shaft is displaceable in an axial direction relative to the housing pipe; and
a lock member that includes:
a base unit fixed on an inner surface of the housing pipe,
at least one elastically deformable arm unit protruding in a base end direction from the base unit,
at least one engaging unit that extends from the at least one arm unit at a first radial side of the shaft, is curved so as to extend around the shaft, and is releasably engaged with the shaft at a second radial side of the shaft, and
at least one engagement release unit that extends from the at least one arm unit and protrudes to an outside of the housing pipe through at least one side hole of the housing pipe, the lock member being fixed in the housing pipe,
wherein the shaft is slidable in the housing pipe from (i) a first position at which the front end of the needle body protrudes from the housing pipe by a predetermined length and the front end of the shaft is located in the second tube to (ii) a second position at which the front end of the needle body is located in the housing pipe, wherein, when the at least one engaging unit is engaged with the shaft, the shaft is held at the first position in the housing pipe, and wherein, when the at least one engagement release unit is pressed inward, displacement of the at least one engaging unit in a direction away from the shaft releases the engagement of the at least one engaging unit with the shaft;

and performing a blood collection using the medical needle.

18. A method comprising:

providing a medical needle comprising:
- a needle body including a needle tip on a front end of the needle body;
- a shaft provided on a base end of the needle body;
- a housing pipe including a first tube, and a second tube that is provided on a base end of the first tube, the shaft being located in the housing pipe such that the shaft is displaceable in an axial direction relative to the housing pipe; and
- a lock member that includes:
  - a base unit fixed on an inner surface of the housing pipe,
  - at least one elastically deformable arm unit protruding in a base end direction from the base unit,
  - at least one engaging unit that extends from the at least one arm unit at a first radial side of the shaft, is curved so as to extend around the shaft, and is releasably engaged with the shaft at a second radial side of the shaft, and
  - at least one engagement release unit that extends from the at least one arm unit and protrudes to an outside of the housing pipe through at least one side hole of the housing pipe, the lock member being fixed in the housing pipe, wherein the shaft is slidable in the housing pipe from (i) a first position at which the front end of the needle body protrudes from the housing pipe by a predetermined length and the front end of the shaft is located in the second tube to (ii) a second position at which the front end of the needle body is located in the housing pipe, wherein, when the at least one engaging unit is engaged with the shaft, the shaft is held at the first position in the housing pipe, and wherein, when the at least one engagement release unit is pressed inward, displacement of the at least one engaging unit in a direction away from the shaft releases the engagement of the at least one engaging unit with the shaft;

and performing a blood infusion using the medical needle.

19. A method comprising:

providing a medical needle comprising:
- a needle body including a needle tip on a front end of the needle body;
- a shaft provided on a base end of the needle body;
- a housing pipe including a first tube, and a second tube that is provided on a base end of the first tube, the shaft being located in the housing pipe such that the shaft is displaceable in an axial direction relative to the housing pipe; and
- a lock member that includes:
  - a base unit fixed on an inner surface of the housing pipe,
  - at least one elastically deformable arm unit protruding in a base end direction from the base unit,
  - at least one engaging unit that extends from the at least one arm unit at a first radial side of the shaft, is curved so as to extend around the shaft, and is releasably engaged with the shaft at a second radial side of the shaft, and
  - at least one engagement release unit that extends from the at least one arm unit and protrudes to an outside of the housing pipe through at least one side hole of the housing pipe, the lock member being fixed in the housing pipe, wherein the shaft is slidable in the housing pipe from (i) a first position at which the front end of the needle body protrudes from the housing pipe by a predetermined length and the front end of the shaft is located in the second tube to (ii) a second position at which the front end of the needle body is located in the housing pipe, wherein, when the at least one engaging unit is engaged with the shaft, the shaft is held at the first position in the housing pipe, and wherein, when the at least one engagement release unit is pressed inward, displacement of the at least one engaging unit in a direction away from the shaft releases the engagement of the at least one engaging unit with the shaft;

and performing a fluid infusion using the medical needle.

* * * * *